US009803927B2

(12) United States Patent
Young

(10) Patent No.: US 9,803,927 B2
(45) Date of Patent: Oct. 31, 2017

(54) APPARATUS FOR PREPARING A SELF-CONTAINED HEATED TREATMENT RECEPTACLE FOR USE BY A SUBJECT

(75) Inventor: Daniel L. Young, Henderson, NV (US)

(73) Assignee: Forever Young International, Inc., Henderson, NV (US)

(*) Notice: Subject to any disclaimer, the term of this patent is extended or adjusted under 35 U.S.C. 154(b) by 485 days.

(21) Appl. No.: 13/816,824

(22) PCT Filed: Aug. 13, 2010

(86) PCT No.: PCT/US2010/045435
§ 371 (c)(1),
(2), (4) Date: Apr. 16, 2013

(87) PCT Pub. No.: WO2012/021135
PCT Pub. Date: Feb. 16, 2012

(65) Prior Publication Data
US 2013/0280666 A1  Oct. 24, 2013

(51) Int. Cl.
*F27D 5/00* (2006.01)
*A45D 26/00* (2006.01)
(Continued)

(52) U.S. Cl.
CPC ........... *F27D 5/00* (2013.01); *A45D 26/0014* (2013.01); *A45D 29/00* (2013.01); *A45D 40/00* (2013.01); *A61F 7/0241* (2013.01); *A61F 7/03* (2013.01); *A45D 2200/155* (2013.01); *A61F 2007/0036* (2013.01); *A61F 2007/0276* (2013.01); *A61F 2007/0292* (2013.01)

(58) Field of Classification Search
USPC ...................................... 432/253; 126/263.07
See application file for complete search history.

(56) References Cited

U.S. PATENT DOCUMENTS 3,297,386 A * 1/1967 Stanek .................... A47J 39/02
                                                        312/270.3
3,683,889 A   8/1972 Hoffman
(Continued)

FOREIGN PATENT DOCUMENTS

FR      WO 9856275 A1 * 12/1998 ......... A45D 26/0014
WO          03021158 A2    3/2003
(Continued)

OTHER PUBLICATIONS

International Bureau, International Search Report for International Application No. WO2012021135, dated Feb. 16, 2012, pp. 1-2, Geneva, Switzerland.
(Continued)

*Primary Examiner* — Nathaniel Herzfeld
(74) *Attorney, Agent, or Firm* — Troutman Sanders LLP

(57) ABSTRACT

A self-contained heated wax treatment apparatus includes an outer shell and a rack disposed inside the outer shell. The rack includes a receptacle holder and at least one heater holder. At least a first receptacle is mounted to the receptacle holder of the rack. The first receptacle contains a heat activated substance. A heater is mounted to the heater holder of the rack in thermal conductive contact with the first receptacle. Activation of the heater causes heat to flow to the first receptacle and activate the heat activated substance inside the receptacle.

19 Claims, 20 Drawing Sheets

(51) Int. Cl.
*A45D 29/00* (2006.01)
*A45D 40/00* (2006.01)
*A61F 7/02* (2006.01)
*A61F 7/03* (2006.01)
*A61F 7/00* (2006.01)

(56) References Cited

U.S. PATENT DOCUMENTS

| | | | |
|---|---|---|---|
| 3,969,025 A * | 7/1976 | Brodie | A47L 13/30 219/230 |
| 4,559,921 A | 12/1985 | Benmussa | |
| 4,926,843 A | 5/1990 | Vocke et al. | |
| 5,219,237 A * | 6/1993 | Zonneveld | A45D 26/0014 401/1 |
| 5,220,909 A | 6/1993 | Pickard et al. | |
| 5,279,574 A * | 1/1994 | Forren | A61M 25/02 128/879 |
| 5,611,329 A | 3/1997 | Lamensdorf | |
| 5,891,116 A * | 4/1999 | Mast | 604/290 |
| 5,935,486 A * | 8/1999 | Bell | A47J 36/28 126/263.01 |
| 5,980,144 A * | 11/1999 | DeBourg | A45D 26/0014 401/1 |
| 5,984,953 A | 11/1999 | Sabin et al. | |
| 6,060,691 A * | 5/2000 | Minami | F16K 49/002 137/341 |
| 6,289,889 B1 * | 9/2001 | Bell et al. | 126/263.07 |
| 6,539,935 B2 | 4/2003 | Ichikawa et al. | |
| 6,681,772 B2 * | 1/2004 | Atwater | A61B 90/04 128/878 |
| 6,935,535 B2 | 8/2005 | Pandolfi et al. | |
| 7,161,120 B1 | 1/2007 | Stroud et al. | |
| 7,315,691 B1 | 1/2008 | Palkie et al. | |
| 7,951,123 B2 * | 5/2011 | Donovan et al. | 604/292 |
| 2002/0017310 A1 * | 2/2002 | Gruenbacher et al. | 132/320 |
| 2003/0083722 A1 * | 5/2003 | Cordani et al. | |
| 2006/0005827 A1 * | 1/2006 | Consoli | F24J 1/00 126/263.06 |
| 2006/0289521 A1 | 12/2006 | Bohme et al. | |
| 2007/0125362 A1 | 6/2007 | Ford et al. | |
| 2009/0090351 A1 * | 4/2009 | Sunol | F24J 1/00 126/263.08 |
| 2009/0227967 A1 * | 9/2009 | Donovan | A61M 35/00 604/291 |
| 2009/0280043 A1 * | 11/2009 | Ferguson | 422/236 |
| 2009/0293859 A1 * | 12/2009 | Coffey | F24J 1/00 126/263.01 |
| 2010/0065081 A1 * | 3/2010 | Vracknos | A45D 44/002 132/320 |

FOREIGN PATENT DOCUMENTS

WO   WO 2006/042294        4/2006
WO   WO 2006042294 A2 *   4/2006

OTHER PUBLICATIONS

International Bureau, Written Opinion of the International Search Authority for International Application No. WO2012021135, dated Feb. 13, 2013, pp. 1-7, Geneva, Switzerland.
International Bureau, International Preliminary Report on Patentability Chapter I for International Application No. WO2012021135, dated Feb. 19, 2013, pp. 1-8, Geneva, Switzerland.
Communication under Rule 71(3) EPC dated Feb. 20, 2017, from corresponding European application serial No. 10855984.0.
Decision to grant a European patent pursuant to Article 97(1) EPC dated Jul. 6, 2017, from corresponding European application serial No. 10855984.0.

* cited by examiner

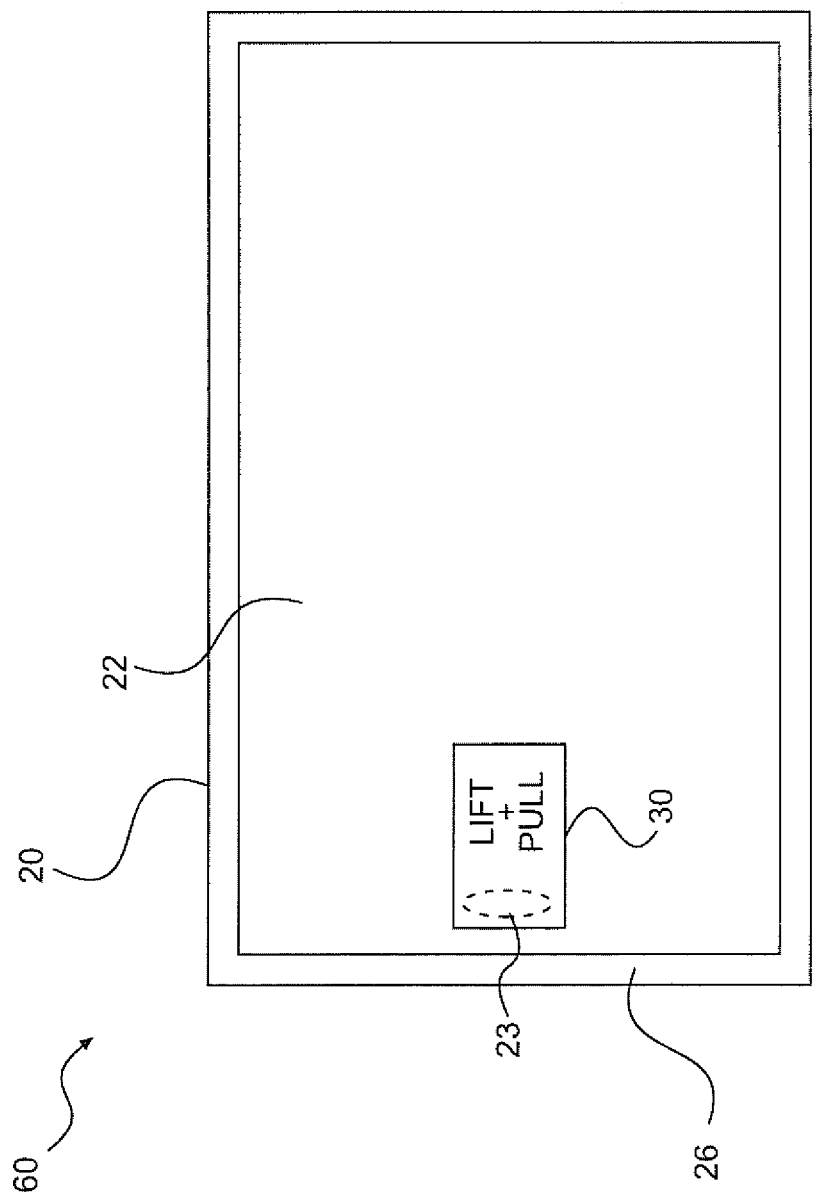

APPARATUS FOR PREPARING A SELF-CONTAINED HEATED TREATMENT RECEPTACLE FOR USE BY A SUBJECT

CROSS-REFERENCE TO RELATED APPLICATIONS

This application is a United States national stage entry of International Application Serial No. PCT/US2010/045435 filed Aug. 13, 2010, the contents of which are incorporated herein by reference in their entirety as if set forth verbatim.

FIELD

The following description relates generally to devices for heating heat activated substances, and more particularly to a self-contained heated wax treatment apparatus.

BACKGROUND

For many years, the only manner in which personal skincare items in the spa market could be warmed or heated was by utilizing an external heat source. Typically, this source was a pot of boiling or hot water, an electric heating apparatus or other basic heating sources. In either case, while the warmth was certainly available for use, the risk of having that heating apparatus in the proximity of spa guests was significant. For instance, a spa guest could easily be scalded by hot water, and the danger of using electrical appliances in spa-type environments is widely known.

Another drawback to conventional methods of heating therapeutic substances for skincare treatments in spas is sanitation. For example, in many conventional therapeutic wax treatments, the wax is heated in a large vessel in which many different users dip their hands/feet in succession. Thus, after the first user undergoes the wax treatment, the wax in the vessel becomes contaminated by the dead skin cells, bacteria and dirt on the user's hand/foot. Each successive person to undergo the wax treatment further contaminates the common wax supply in the vessel. Thus, there is a need for individual disposable wax receptacles so that the wax is not contaminated by multiple users. Further, there is a need for an apparatus to safely heat such receptacles to a temperature above the melting point of the wax.

SUMMARY

The embodiments of a self-contained heated wax therapy apparatus disclosed below solve the foregoing problems. The following simplified summary is provided in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

In one aspect of the disclosed embodiments, a self-contained heated wax treatment apparatus includes an outer shell and a rack disposed inside the outer shell. The rack includes a receptacle holder and at least one heater holder. At least a first receptacle is mounted to the receptacle holder of the rack. The first receptacle contains a heat activated substance. A heater is mounted to the heater holder of the rack in thermal conductive contact with the first receptacle. Activation of the heater causes heat to flow to the first receptacle and activate the heat activated substance inside the receptacle.

The outer shell may comprise two halves hingedly connected to each other so as to expose the rack when the two halves of the outer shell are spread apart and conceal the rack when the two halves of the outer shell are closed. The rack may be hingedly connected to the outer shell. A second receptacle may be mounted to the receptacle holder of the rack in thermal conductive contact with the heater. The second receptacle may also contain a heat activated substance. The rack may be removable from the outer shell rather than hingedly connected thereto. For example, the rack may be slidably disposed inside the outer shell.

In some embodiments, the first receptacle is a heat therapy receptacle such as a glove. The heat activated substance in the first receptacle may be a solid that melts after the heater is activated, for example a wax such as paraffin. The heat activated substance may have a melting point temperature above which it becomes a liquid that drains to the bottom of the first receptacle where it is stored at a temperature not greater than 5° C. above the melting point temperature of the heat activated substance. This may be the case even when the heater is maintained at a temperature not less than 25° C. above the melting point temperature of the heat activated substance.

The outer shell may include compression members that compress the first receptacle against the heater. The heater may be a heater pouch containing an exothermic reactant. The heater pouch may also contain an activator separated from the exothermic reactant by a breakable barrier. This breakable barrier may be shearable by pulling on a tab connected to the breakable barrier and extending outside of the heater pouch. Alternatively, the breakable barrier may be frangible. The activator may be a liquid such as water or an electrolyte solution.

The heater pouch may further comprise a vent for expelling gases after activation of the exothermic reactant. The vent may comprise, or may be replaced by, a pressure regulator that regulates expulsion of gases from the heater pouch to maintain a target gas pressure inside the heater pouch while the exothermic reactant reacts with the activator. The heater pouch may comprise at least one outer wall that presses against the first receptacle when the heater pouch is inflated to the target air pressure. The heater pouch may comprise at least two leaves, and the heater pouch may be mounted to the heater holder of the rack with the first receptacle between the at least two leaves of the heater pouch.

The first receptacle may include at least two internal compartments separated by a barrier permeable to the heat activated substance after the heat activated substance is activated. The barrier permeable to the heat activated substance may be a perforation line.

The rack may include at least one collector chamber below the receptacle for holding the heat activated substance inside the first receptacle after the heat activated substance is activated. The receptacle holder of the rack may include one or more flanges, and the first receptacle may include a pocket that is hangable on the flange of the receptacle holder. The rack may also include an inner chamber that is the heater holder. Finally, the shell may include an aperture for venting gases.

To the accomplishment of the foregoing and related ends, certain illustrative aspects are described herein in connection with the following description and the annexed drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

FIG. 7 is a front view of another embodiment of a heater.

DETAILED DESCRIPTION

In one aspect of the disclosed embodiments, a self contained heated wax therapy treatment apparatus comprises a rack disposed inside an outer shell. The rack has at least one receptacle holder and a heater holder. A receptacle containing a heat activated substance is mounted to the receptacle holder and a heater is mounted to the heater holder with the heater in thermally conductive contact with the receptacle. When the heater is activated, heat flows from the heater into the receptacle thereby activating the heat activated substance inside the receptacle. The heat activated substance may be a wax or resin that melts when heat is applied.

Figure 1:
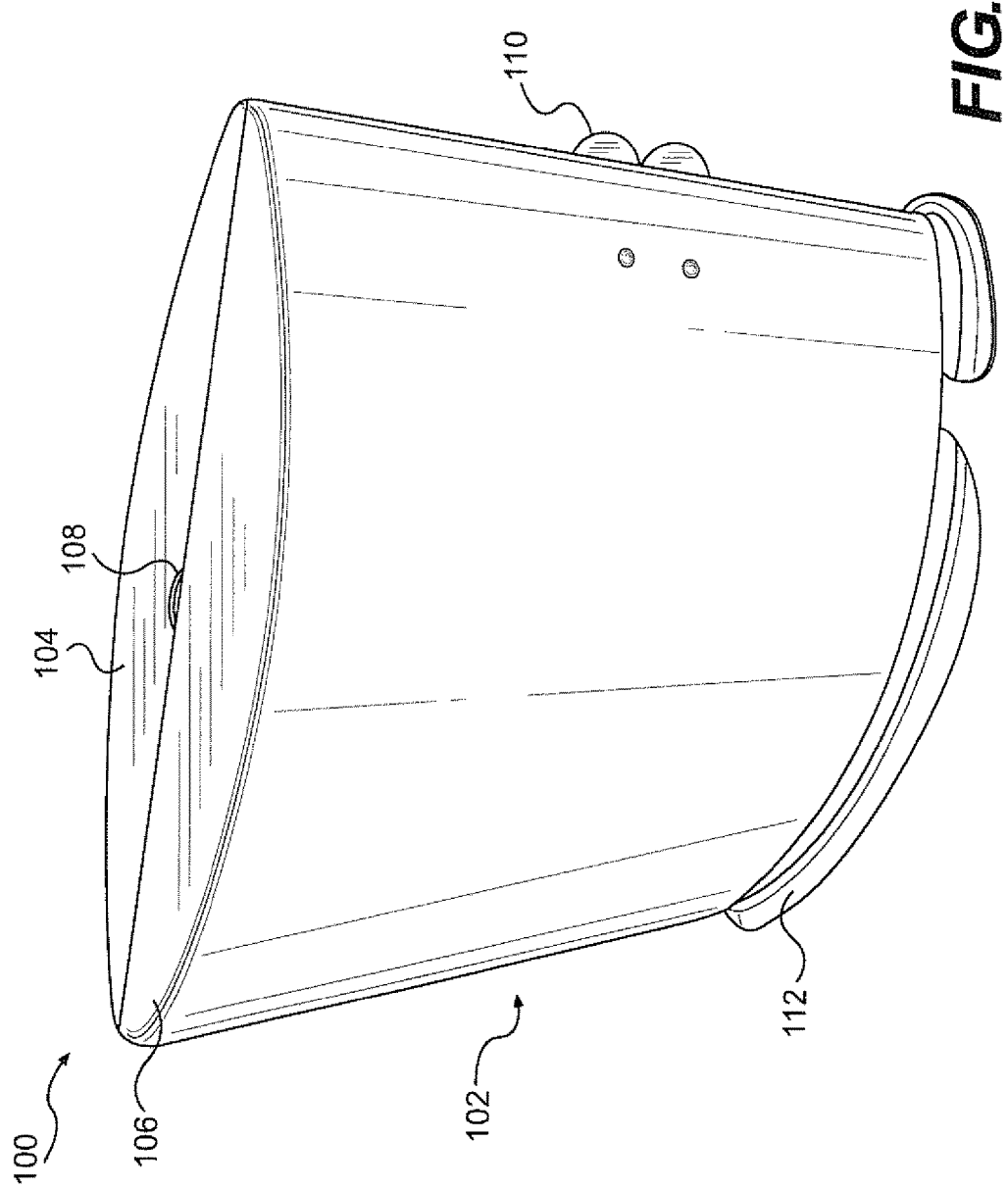
FIG. 1 is a perspective view of one embodiment of a self-contained heated wax therapy treatment apparatus.

FIG. 1 is a perspective view of one embodiment of a heated wax therapy treatment apparatus. Heated wax therapy treatment apparatus 100 includes outer shell 102 which, in this embodiment, comprises first half-shell 104 and second half-shell 106. First half-shell 104 and second half-shell 106 are hingedly connected to one another in a clamshell manner. Outer shell 102 also includes vent 108 which is used for a purpose to be described below. On the side of outer shell 102 opposite the hinged connection of first half-shell 104 to second half-shell 106 are tabs 110 which are used to open outer shell 102 by spreading apart first and second half-shells 104 and 106. Finally, outer shell 102 includes pedestal 112 which provides vertical stability to outer shell 102. Pedestal 112 may be formed integrally with first half-shell 104 or second half-shell 106.

Figure 2:
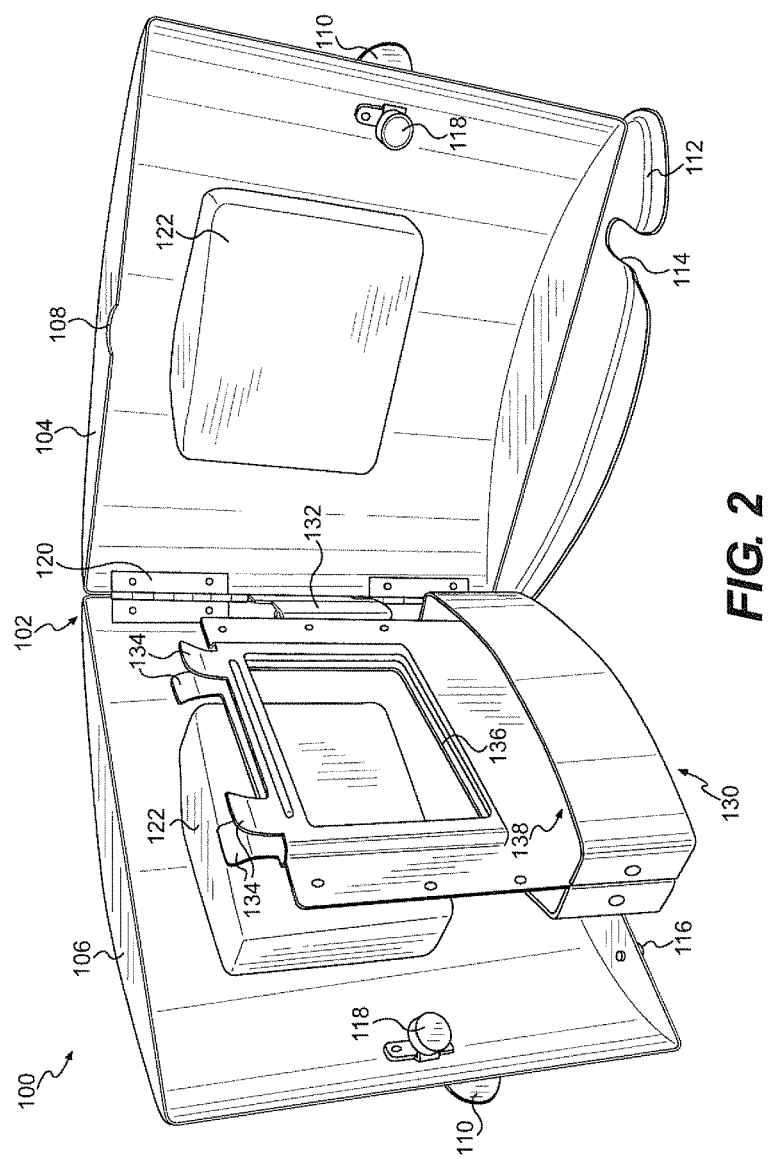
FIG. 2 is a perspective view of the self-contained heated wax therapy treatment apparatus of FIG. 1 shown with the outer shell opened.
Figure 3:
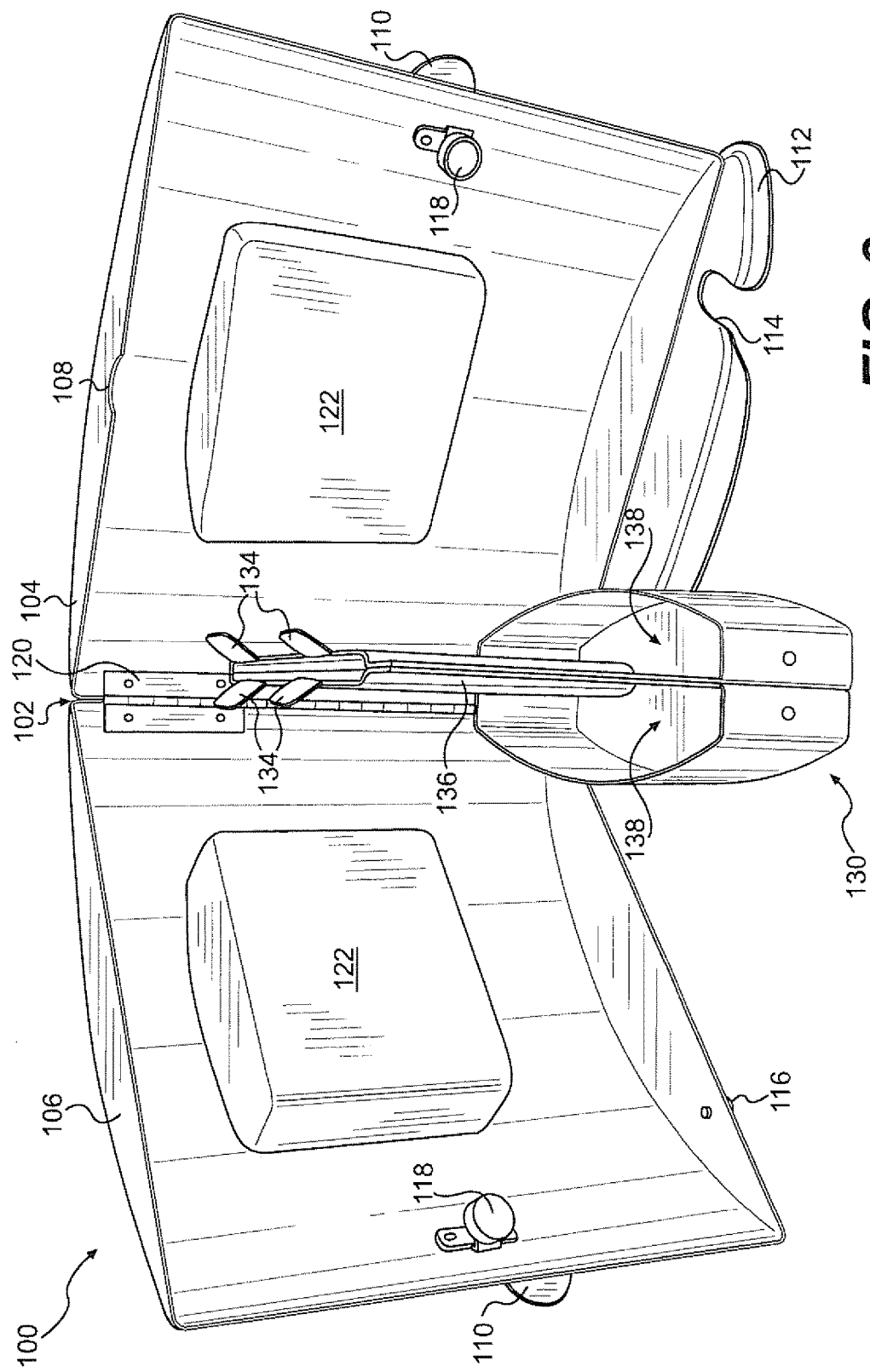
FIG. 3 is a perspective view of the self-contained heated wax therapy treatment apparatus of FIG. 1 shown with the outer shell opened and the rack at an alternate angle with respect to the outer shell.
Figure 4:
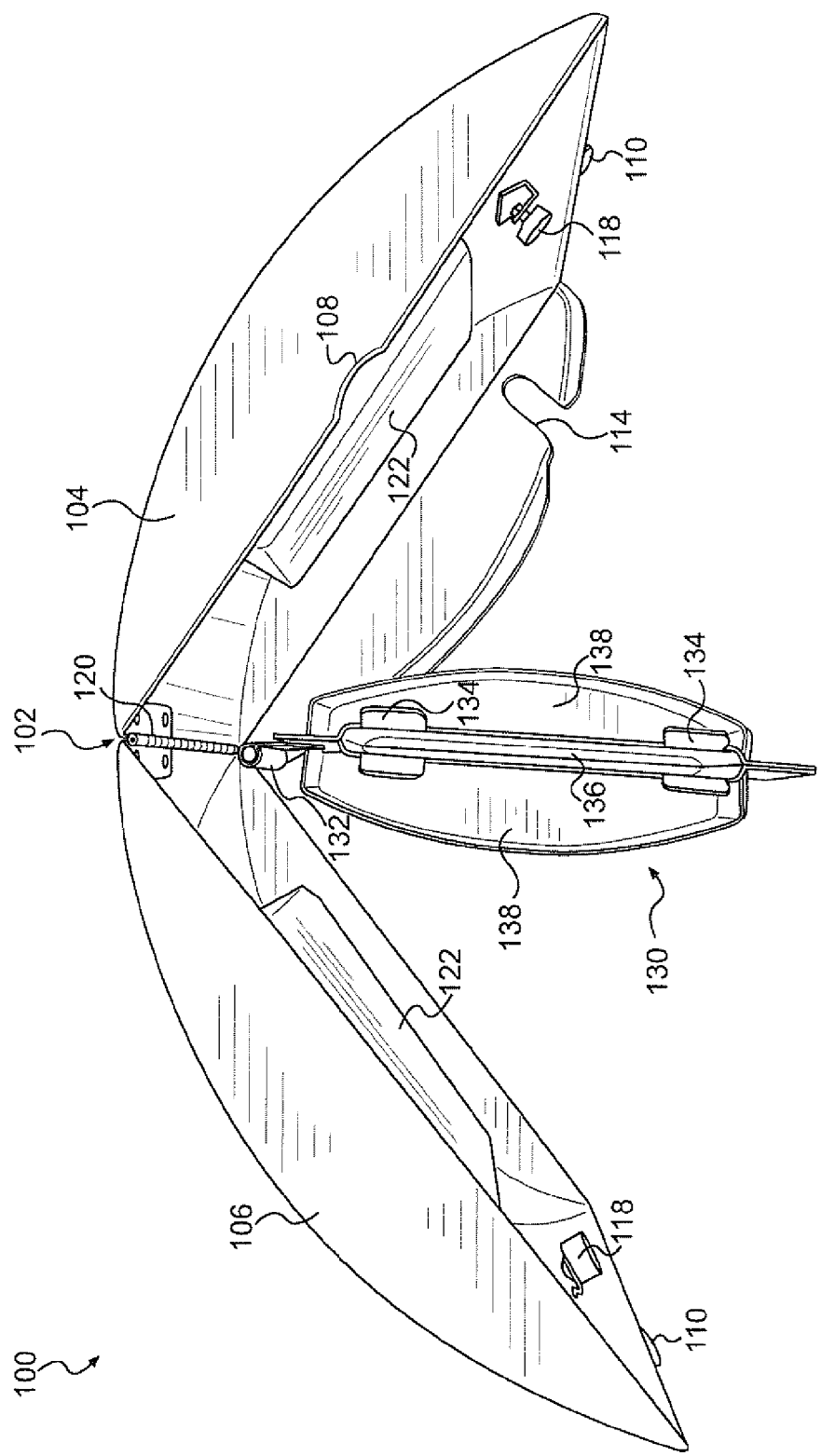
FIG. 4 is a top view of the self-contained heated wax therapy treatment apparatus of FIG. 1 shown with the outer shell opened.

FIGS. 2-4 show three views of the inside of outer shell 102 after first and second half-shells 104 and 106 have been spread apart. First half-shell 104 includes pin 116 which is engageable with slot 114 in second half-shell 106. The engagement of pin 116 in slot 114 helps to align first and second half-shells 104 and 106 when outer shell 102 is closed. First and second half-shells 104 and 106 each include at least one clasp 118. Clasps 118 may be magnets or any other releasable locking mechanism known in the art, for example closures used in cabinetry. First and second half-shells 104 and 106 may also each include compression member 122, which may be a compressible cushion or simply a rigid protrusion on the inner surfaces of first and second half-shells 104 and 106. Finally, it can be seen that hinged connection between first and second half-shells 104 and 106 is provided by hinge 120.

Disposed inside outer shell 102 is rack 130 which may be hingedly connected to outer shell 102 by rack hinge 132. It should be noted, however, that rack 130 is not necessarily hingedly connected to outer shell 102 and may instead be rigidly connected to first half-shell 104 or second half-shell 106. Furthermore, rack 130 may not be connected to outer shell 102 at all and instead may simply rest inside outer shell 102 in a vertical position.

Rack 130 includes at least one receptacle holder 134. In the illustrated embodiment, rack 130 includes two opposing receptacle holders 134 separated by heater holder 136. Receptacle holder 134 may comprise one or more flanges from which a receptacle may be hung. In the illustrated embodiment, each receptacle holder 134 comprises two flanges. However, in other embodiments, receptacle holder 134 may take another form, such as a chamber for holding a receptacle. Heater holder 136 is disposed between the two illustrated receptacle holders 134 and comprises an internal chamber in rack 130 for holding a heater. Finally, rack 130 also may include at least one collector chamber 138 below receptacle holder 134.

Figure 5A:
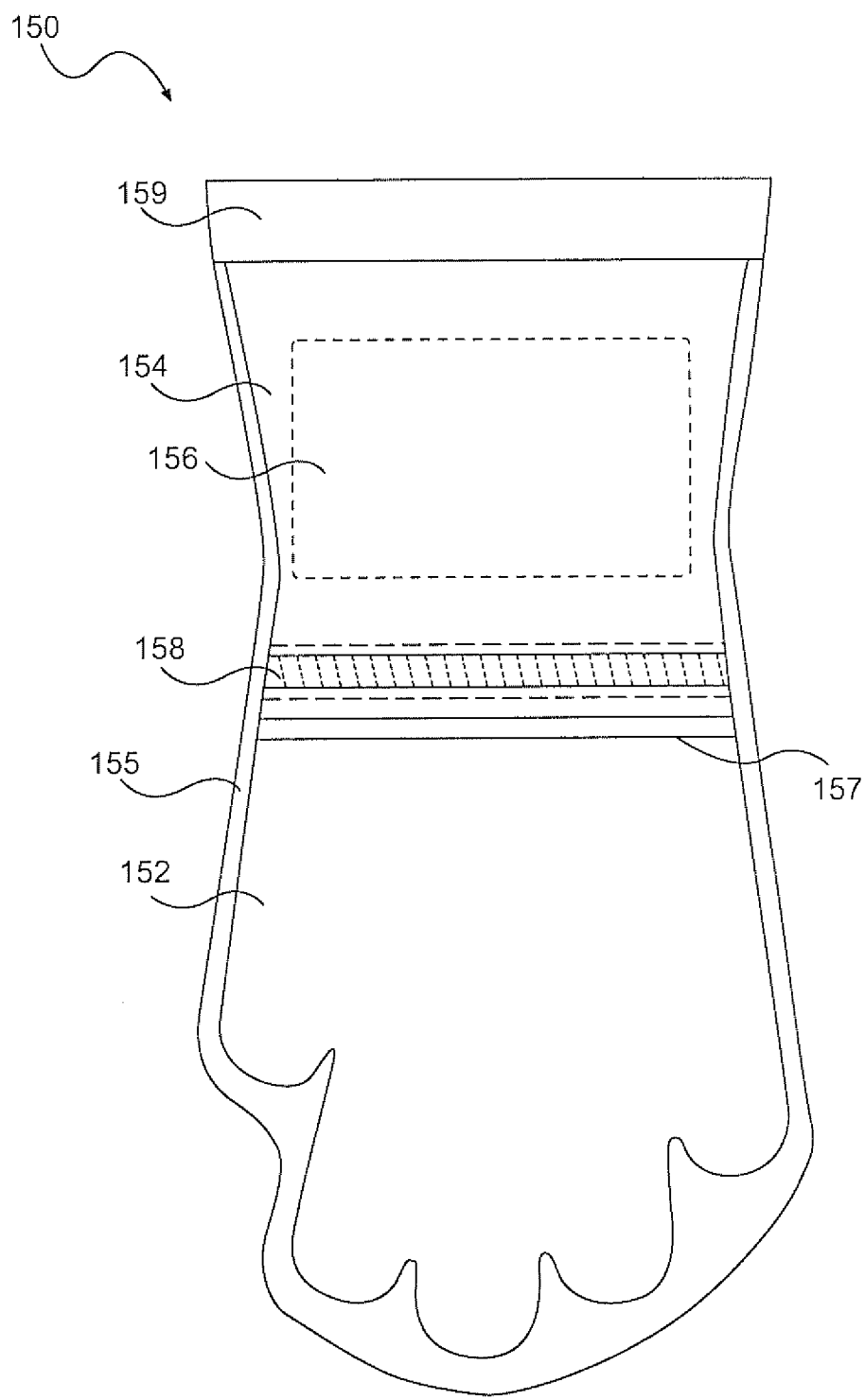
FIG. 5A is a front view of a receptacle for use with a self-contained heated wax therapy treatment apparatus.
Figure 5B:
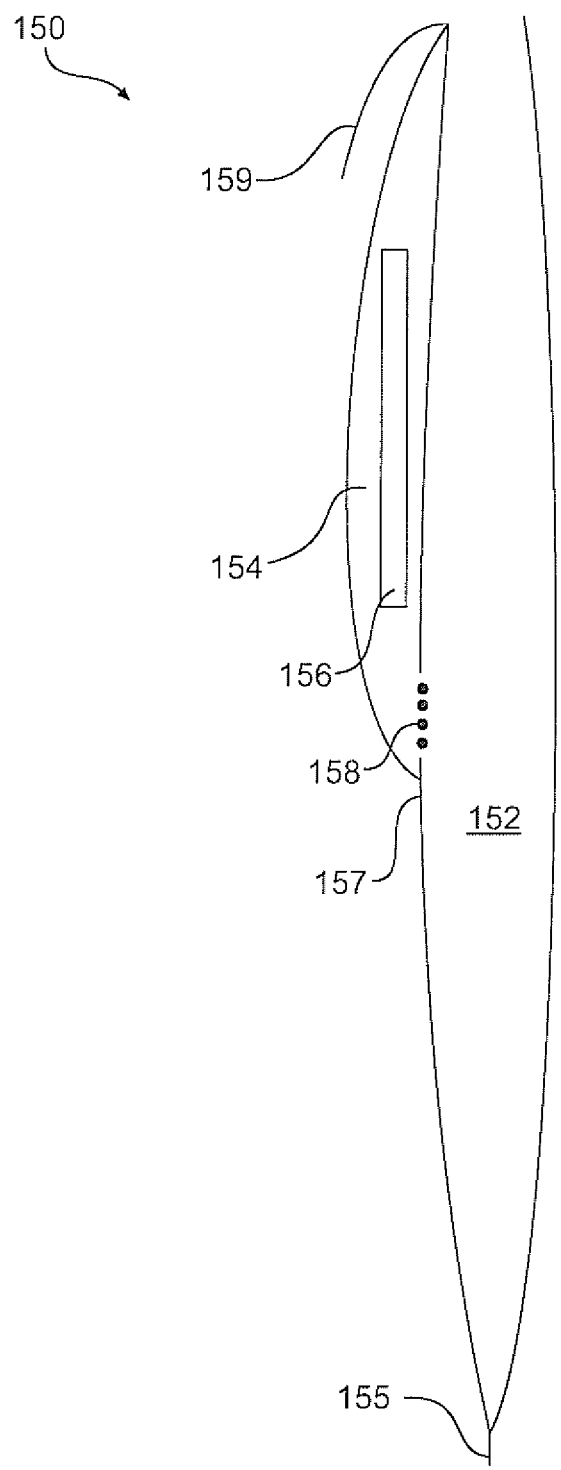
FIG. 5B is a cross-sectional view of the receptacle of FIG. 5A.

Receptacle 150 is shown in FIGS. 5A and 5B. Receptacle 150 includes treatment chamber 152 and substance chamber 154. Substance chamber 154 is disposed adjacent to treatment chamber 152 such that the two chambers share a common wall for the length of substance chamber 154 (see FIG. 5B). The peripheral edges of treatment chamber 152 and substance chamber 154 are sealed by seal 155. Furthermore, the bottom edge of substance chamber 154 (i.e., the edge of substance chamber 154 furthest from the entrance to receptacle 150) is sealed to the outer wall of treatment chamber 152 along transverse seal 157.

Figure 17:
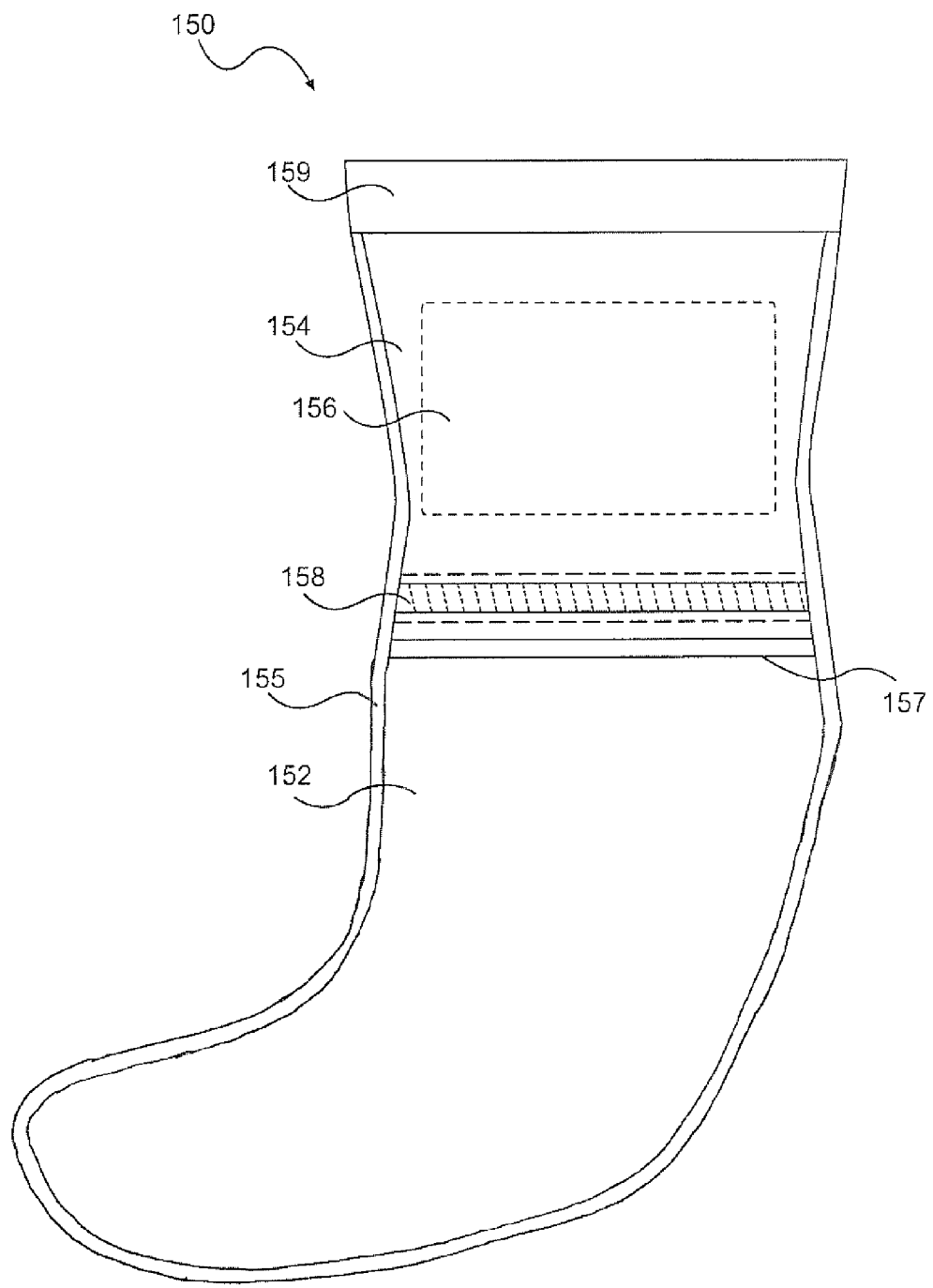
FIG. 17 is a front view of another embodiment of a receptacle for use with a self-contained heated wax therapy treatment apparatus.

It can be seen that in this embodiment receptacle 150 is a glove or mitt and treatment chamber 152 is shaped to accommodate a human hand. However, receptacles of other shapes are also contemplated, for example with treatment chamber 152 shaped to accommodate a human foot or other body part (see FIG. 17). Heat activated substance 156 is disposed inside substance chamber 154. In this embodiment, heat activated substance 154 is a therapeutic wax such as paraffin that is solid at room temperature.

Treatment chamber 152 and substance chamber 154 are separated by permeable barrier 158 which may be a plurality of perforations or apertures. As best visualized with reference to FIG. 5B, if heat activated substance 156 is melted, the melted heat activated substance 156 will flow from substance chamber 154 through permeable barrier 158 and into treatment chamber 152. Finally, receptacle 150 includes flap 159. Flap 159 is attached to receptacle 150 along the upper edge of receptacle 150 (i.e. along the opening of the glove) and along the two opposite edges. Flap 159 thereby forms a pocket along the upper edge of receptacle 150.

To mount receptacle 150 on receptacle holder 134, the pocket formed by flap 159 is placed over the flanges of receptacle holder 134 so that receptacle holder 150 hangs from the top of rack 130 with treatment chamber 152 held in collector chamber 138. As receptacle 150 may be longer than rack 130 is tall, treatment chamber 152 may be "bunched up" inside collector chamber 138. This "bunching up" of treatment chamber 152 ensures that once heat activated substance 156 melts it does not all simply collect at the lowest point of treatment chamber 152 and instead is relatively evenly distributed inside treatment chamber 152.

Figure 6A:
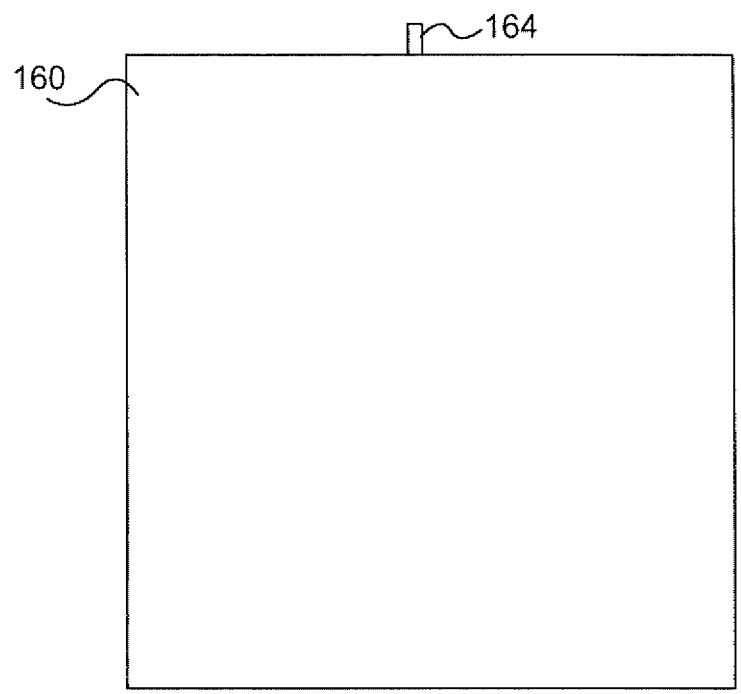
FIG. 6A is a front view of one embodiment of a heater for use with a self-contained heated wax therapy treatment apparatus.
Figure 6B:
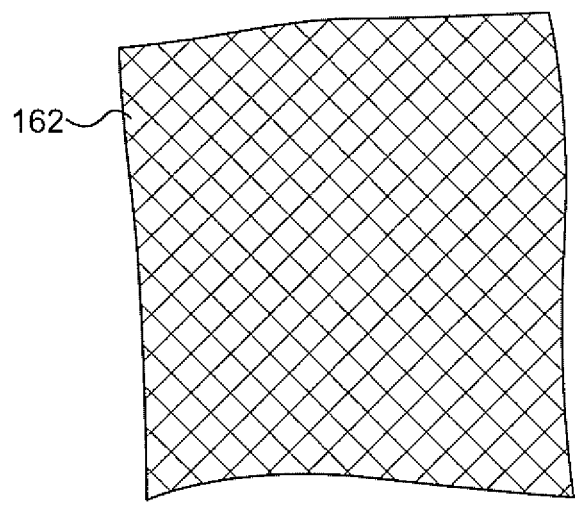
FIG. 6B is a front view of one embodiment of a reactant compartment for insertion inside the heater of FIG. 6A.

One embodiment of heater 160 is shown in FIGS. 6A and 6B. In this embodiment, heater 160 is an impermeable pouch that holds a reactant which is stored in permeable pouch 162. Permeable pouch 162 may include cross-stitching which forms a plurality of small chambers. Where the reactant is a powder, these chambers ensure that the reactant does not collect at one end of permeable pouch 162 and instead remains relatively evenly distributed inside permeable pouch 162. Permeable pouch 162 is disposed inside the impermeable pouch of heater 160. Heater 160 may simply have an open upper end or may instead comprise pressure regulator 164. Pressure regulator 164 maintains a predetermined pressure inside the impermeable pouch of heater 160 after an activator is added to the reactant inside permeable pouch 162 and an exothermic reaction releases reaction gases which escape in a controlled manner through pressure regulator 164.

When heater 160 is activated, it begins to heat heat activated substance 156. Where heat activated substance 156 has a melting point below the temperature of the surface of heater 160, heat activated substance 156 will melt. It is notable that once heat activated substance 156 melts, it immediately drains from substance chamber 154 through permeable barrier 158 and into treatment chamber 152. This is a notable advantage because it prevents heat activated substance 156 from being overheated to possibly dangerous temperatures. Once heat activated substance drains to the bottom of receptacle 150, it is no longer in thermal conductive contact with heater 160 because melted heat activated substance 156 is now disposed below heater 160 at the bottom of receptacle 150 inside collector chamber 138. In one embodiment, heat activated substance 156 is not heated substantially beyond its melting point even though the surface of heater 160 may be at a temperature greater than 20° C. above the melting point of heat activated substance 156.

In one embodiment, the activator added to heater 160 to cause an exothermic reaction with the reactant inside heater 160 is a liquid such as water or an electrolyte solution. The activator may simply be poured into the upper end of heater 160. However, in another embodiment of a heater, such as heater 60 illustrated in FIGS. 7-11, the activator is stored in a shearable compartment which is disposed inside heater 60.

Figure 8:
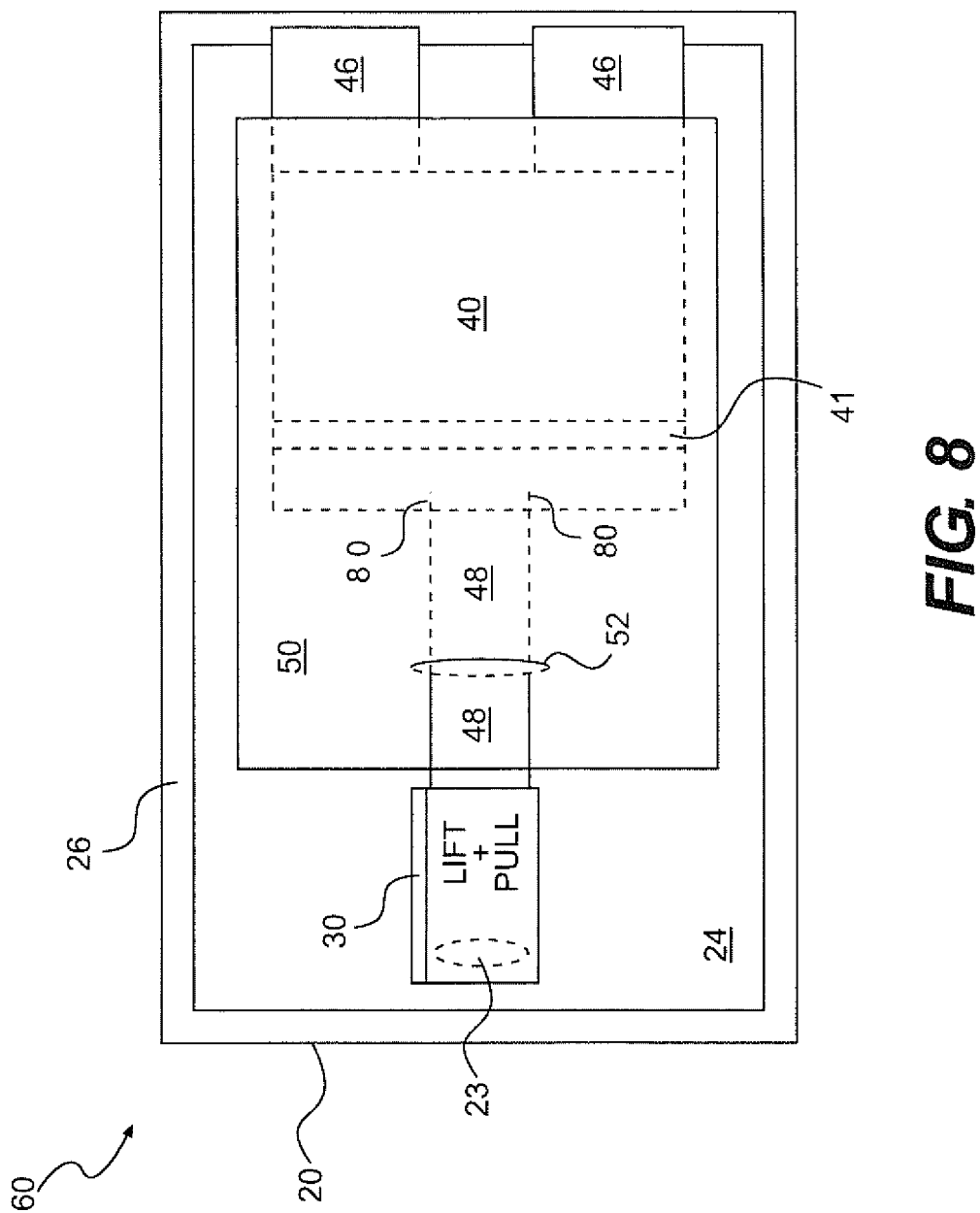
FIG. 8 is a front view of the heater of FIG. 7 with the upper layer removed for clarity.
Figure 9:
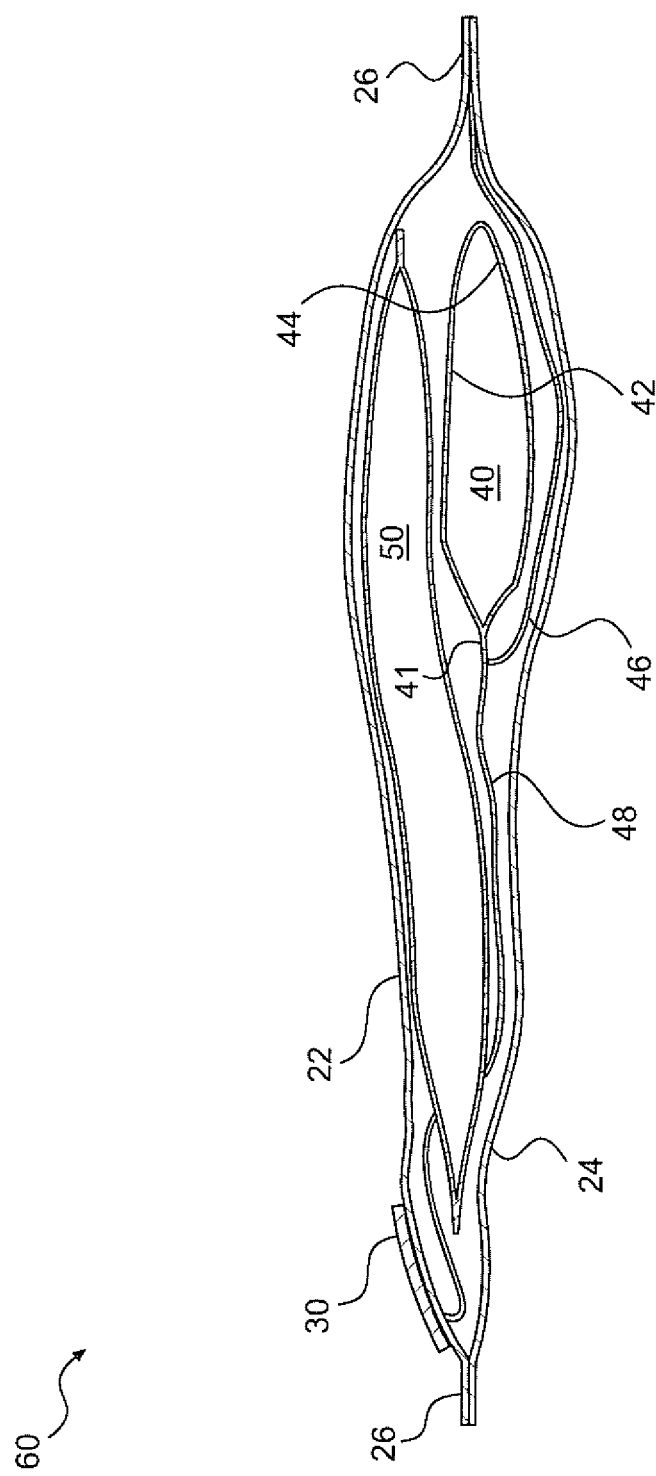
FIG. 9 is a cross-sectional view of the heater of FIG. 7.

In this embodiment, heater 60 includes outer containment envelope 20 which is formed from first layer 22 and second layer 24 (see FIGS. 8 and 9). First layer 22 and second layer 24 are bonded together along the periphery 26 of outer containment envelope 20. The bond between first layer 22 and second layer 24 is air- and watertight so that outer containment envelope 20 is a sealed container. Pull tab 30 is adhered to first layer 22 over slit 23 in first layer 22. Although slit 23 is present in first layer 22, outer containment envelope 20 is nonetheless a sealed container (prior to activation of heater 60) because pull tab 30 is adhered to the surface of first layer 22 all around slit 23 to hermetically seal outer containment envelope 20.

FIG. 8 shows heater 60 with first layer 22 of outer containment envelope 20 removed in order to reveal the contents of heater 60. Sealed activator compartment 40 is shown in hidden lines because it is underneath reactant compartment 50. Sealed activator compartment 40 includes transverse seal 41 which segregates the contents of sealed activator compartment 40 from the inside of outer containment envelope 20. Three strips of material are connected to sealed activator compartment 40 adjacent to transverse seal 41. Two outer strips 46 are folded under sealed activator compartment 40 with their tips fixedly anchored inside outer containment envelope 20 to periphery 26 of outer containment envelope 20. The third strip, middle shear strip 48, extends away from sealed activator compartment 40. The tip of middle shear strip 48 is attached to pull tab 30. Reactant compartment 50 is disposed on top of sealed activator compartment 40 and may include a membrane that is permeable to the activator contained inside sealed activator compartment 40.

As seen in FIGS. 8 and 9, middle shear strip 48 passes through slit 52 in reactant compartment 50 and then through slit 23 in first layer 22 of outer containment envelope 20. If reactant compartment 50 is disposed adjacent to slit 23 inside outer containment envelope 20, reactant compartment 50 forms a barrier or dam that prevents reactants from escaping through slit 23. However, slit 23 nonetheless permits gasses to escape from inside outer containment envelope 20.

Figure 10A:
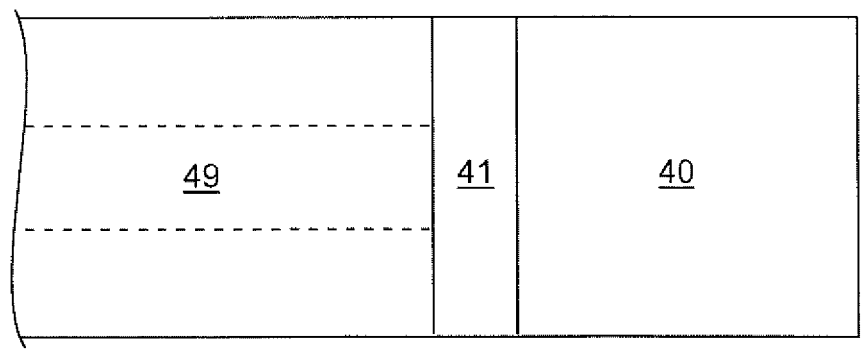
FIG. 10A is a front view of the sealed activator compartment inside the heater of FIG. 7
Figure 10B:
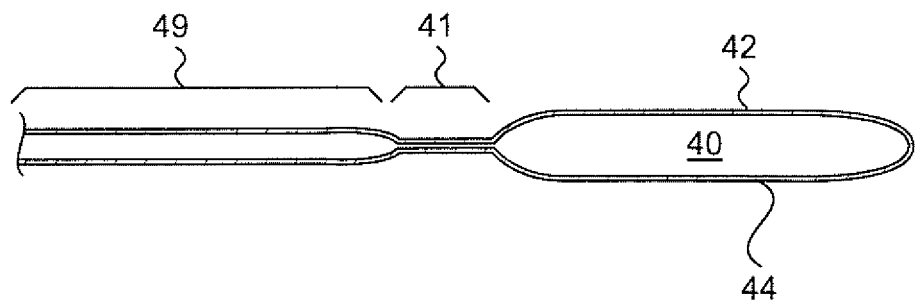
FIG. 10B is a cross-sectional view of the sealed activator compartment of FIG. 10A.

To activate heater 60, the user pulls on pull tab 30 which causes sealed activator compartment 40 to shear open and empty its contents, in a process to be described in further detail below. To understand the pouch activation process, it is instructive to describe the construction of sealed activator compartment 40 with reference to FIGS. 10A-10D. FIG. 10A shows a top view of sealed activator compartment 40 with shearing material 49 connected thereto. Strips 46 and 48 are formed from shearing material 49 in a process described below. Sealed activator compartment 40 and shearing material 49 (and thus, strips 46 and 48 as well) may all be integrally formed with one another, for example from a single sheet of polymeric film that is folded over upon itself and then sealed around its edges and at transverse seal 41. Shearing material 49 may comprise two layers of material corresponding to upper layer 42 and lower layer 44 of sealed activator compartment 40. However, shearing material 49 may also each be formed of a single layer of material.

Figure 10C:
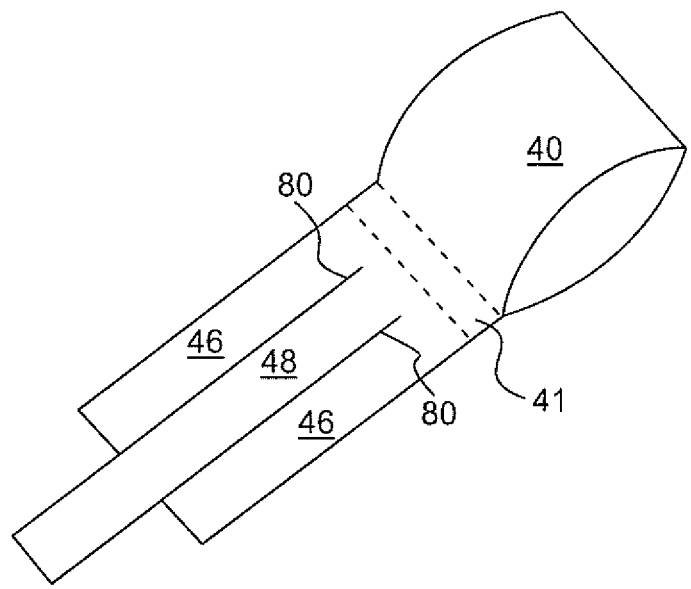
FIG. 10C is a perspective view of the sealed activator compartment of FIG. 10A after three strips are formed.

The dashed lines in FIG. 10A represent pattern lines along shearing material 49. During manufacture of heater 60, shearing material 49 is cut along the dashed pattern lines to form strips 46 and 48, as shown in FIG. 10C. Outer strips 46 are optionally trimmed in length relative to middle strip 48. Between outer strips 46 and middle strip 48 are shear lines 80. As used herein, the term "shear Fine" refers to a cut or tear in a material that will lengthen (i.e. propagate) in generally the same direction as the cut or tear when the material is subjected to shearing forces. Once a cut or tear in a material is established, very little shearing force is required to extend the shear line. As seen in FIG. 10C, sheer lines 80 terminate adjacent transverse seal 41. The region of seal 41 in the path of shear lines 80 is a predetermined failure region of sealed activator compartment 40 because when a user applies shear force to the area (in a process described below) shear lines 80 will lengthen until they shear through transverse seal 41 thereby shearing open sealed activator compartment 40.

Figure 10D:
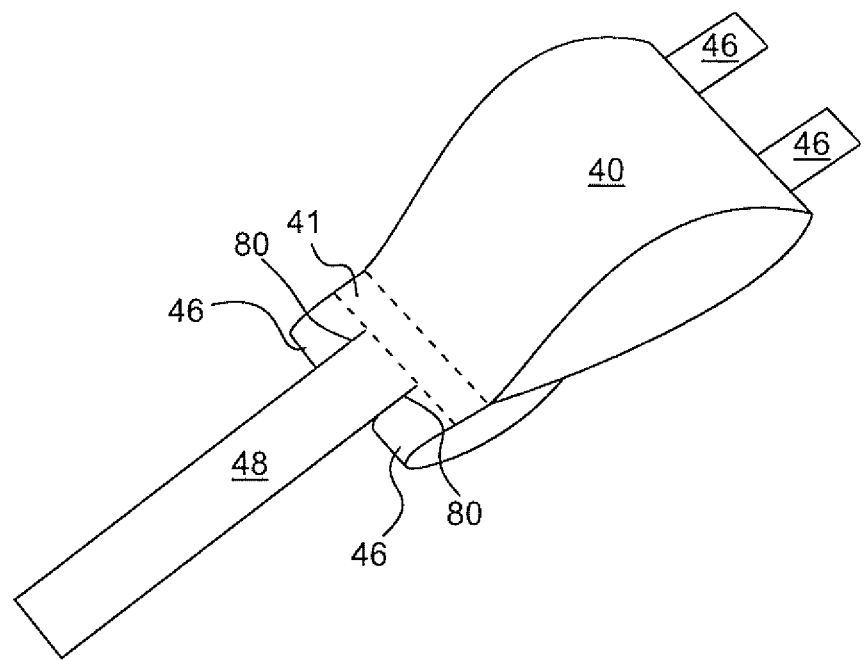
FIG. 10D is a perspective view of the sealed activator compartment of FIG. 10C showing the two outer strips folded under the sealed reactant compartment.

As shown in FIG. 10D, once strips 46 and 48 are formed, outer strips 46 are folded under sealed activator compartment 40, which is then installed into outer containment envelope 20 in this configuration. When sealed activator compartment 40 is installed in outer containment envelope 20, the tips of outer strips 46 are anchored to outer containment envelope 20 so that outer strips 46 remain stationary relative to outer containment envelope 20. Thus, for the purposes of this discussion, outer strips 46 should be viewed as immovable and fixed in place.

Figure 10E:
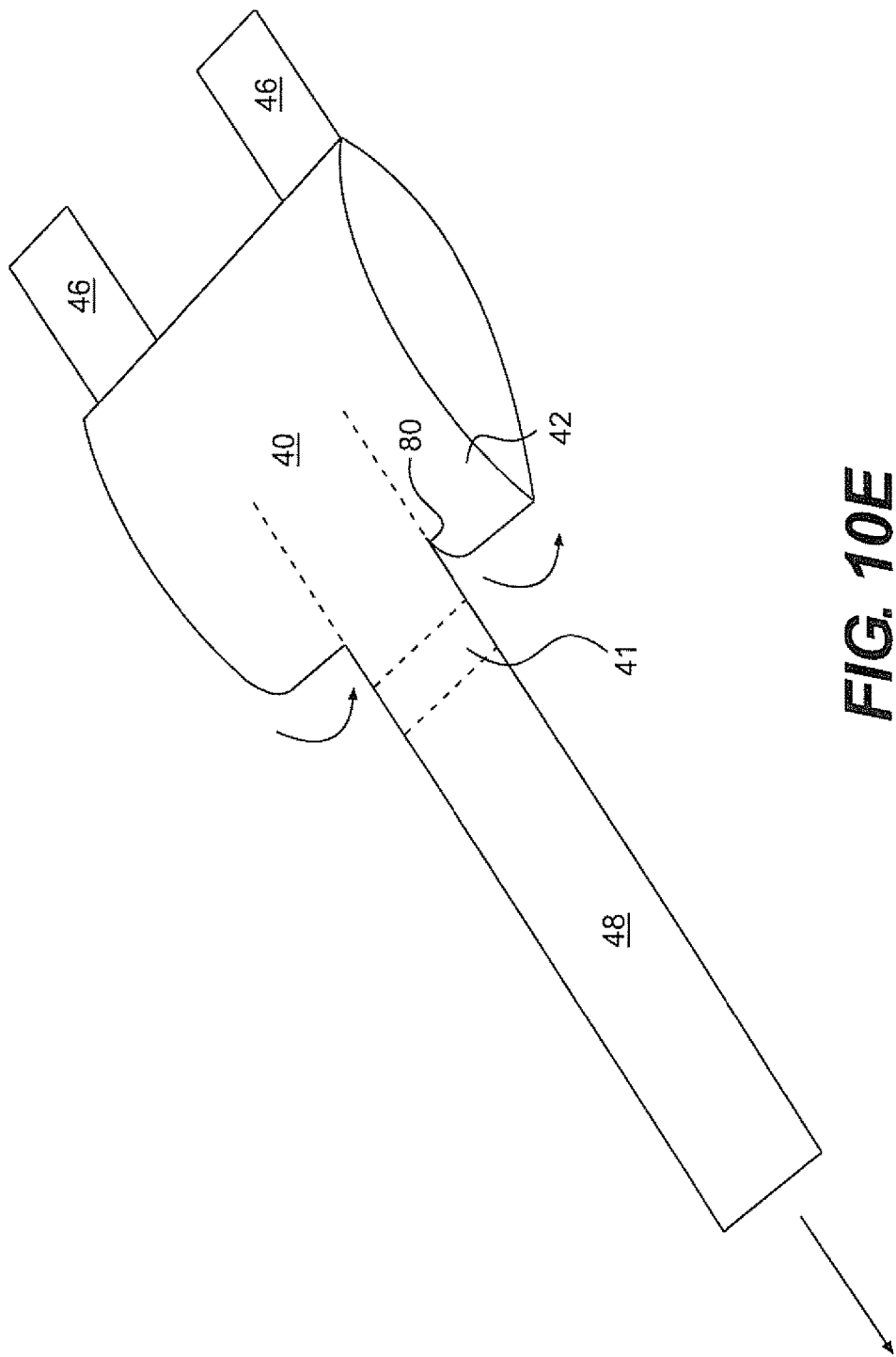
FIG. 10E is a perspective view of the sealed activator compartment of FIG. 10C showing the sealed activator compartment being shorn open by pulling on the middle shear strip.

The process of shearing open sealed activator compartment 40 will now be described with reference to FIG. 10E. The user opens sealed activator compartment 40 (i.e. the user activates heater 60) by pulling on middle strip 48. Because outer strips 46 are anchored in place, the user's pulling force on middle strip 48 is converted into a shearing force along shear lines 80. The counterclockwise arrows in FIG. 10E indicate that as middle strip 48 moves to the left, upper layer 42 of sealed activator compartment 40 in the region above outer strips 46 is caused to "roll over" and shear along shear lines 80. The dotted lines extending from shear lines 80 in FIG. 10E represent the path shear lines 80 will take if the user continues to pull on middle strip 48. Once shear lines 80 completely cross transverse seal 41 in the predetermined failure region, sealed activator compartment 40 is ruptured and its contents are released.

Returning to FIG. 9, once the user pulls on pull tab 30 (which, as explained above, is attached to the tip of middle strip 48), sealed activator compartment 40 will be shorn open and the activator inside sealed activator compartment 40 will be released into outer containment envelope 20 where it contacts a reactant inside reactant compartment 50. In one embodiment, reactant compartment 50 may be permeable pouch 162 (shown in FIG. 6B) which is provided with slit 52 (shown in FIG. 8), then second reactant compartment 50 is permeable to the reactant released from sealed activator compartment 40. Any gases released by the chemical reaction of the first and second reactants may escape through slit 23 in outer containment envelope 20. Furthermore, slit 23 may be provided as a pressure regulating vent that maintains a predetermined pressure inside outer containment envelope 20 of heater 60.

Figure 11:
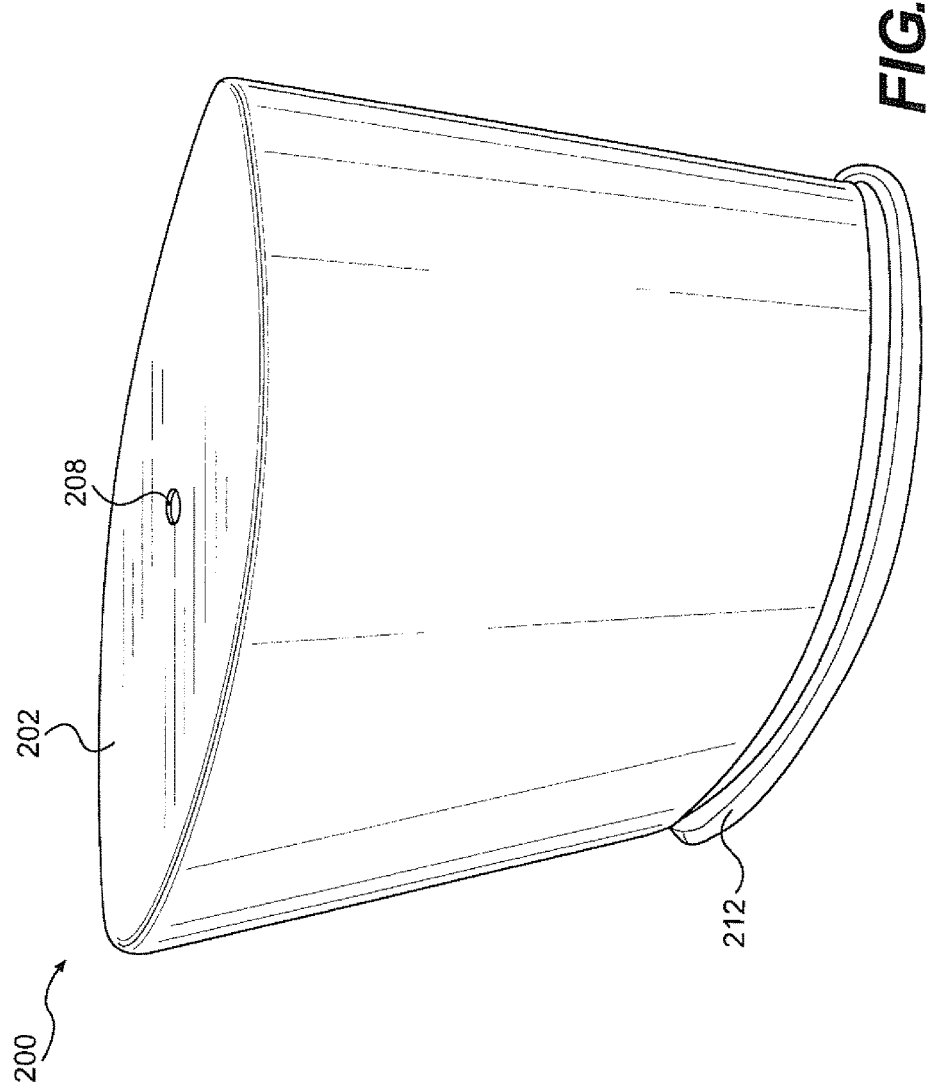
FIG. 11 is a perspective view of another embodiment of a self-contained heated wax therapy treatment apparatus.

Now turning to FIG. 11, another embodiment of a heated wax therapy treatment apparatus is provided. In this embodiment, heated wax therapy treatment apparatus 200 includes outer shell 202 which is provided with vent 208 and pedestal 212. In this embodiment, outer shell 202 is one-piece and does not have two halves that clamshell together. Pedestal 212 may be integrally formed with outer shell 202, in which case the bottom surface of pedestal 212 is open so that outer shell 202 can be placed over rack 230 (shown in FIG. 12) which is not attached to outer shell 202. Alternatively, pedestal 212 may be detachable from outer shell 202, in which case a user lifts outer shell 202 from pedestal 212, places rack 230 on pedestal 212, and then replaces outer shell 202 on pedestal 212 over rack 230. In one embodiment, when outer shell 202 is placed over pedestal 212 a substantially airtight seal is formed between outer shell 202 and pedestal 212. This may be accomplished providing a rubber O-ring between outer shell 202 and pedestal 212.

Figure 12:
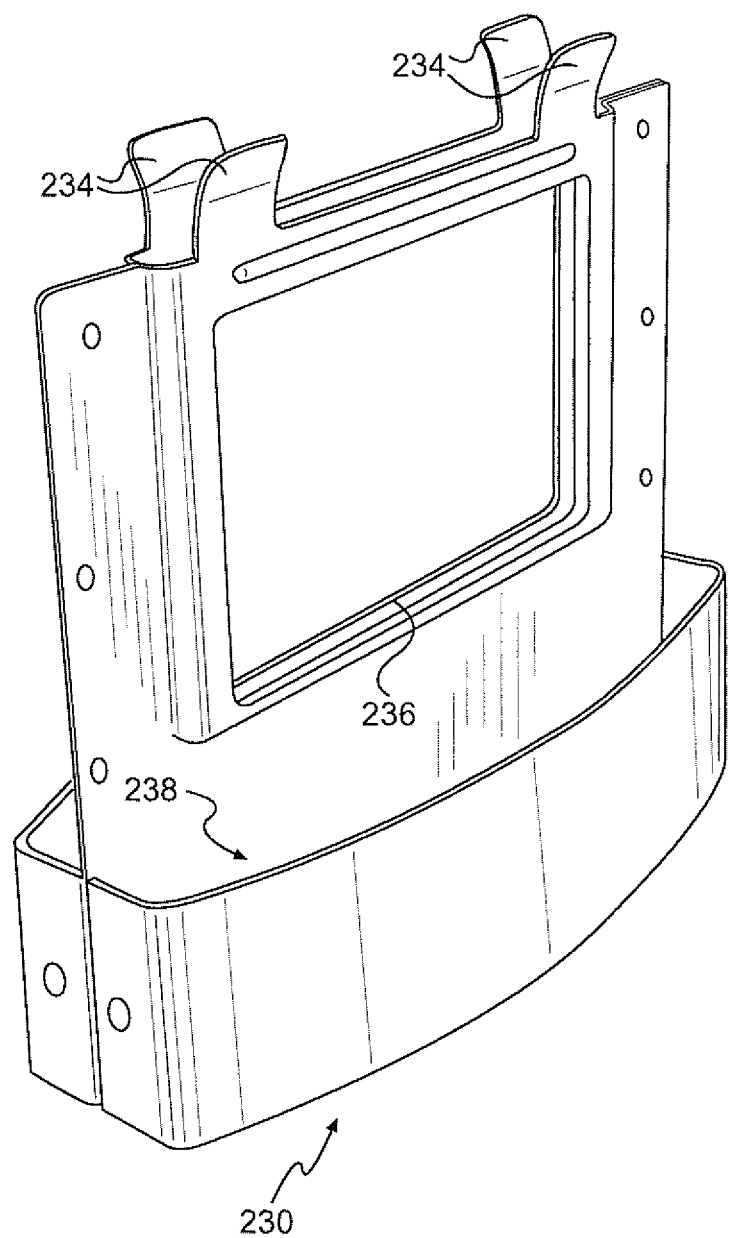
FIG. 12 is a perspective view of a rack for use with the self-contained heated wax therapy treatment apparatus of FIG. 11.

As shown in FIG. 12, rack 230 is substantially identical to rack 130, with the exception that rack 230 is not connected to the inside of outer shell 202. Rack 230 includes at least one receptacle holder 234. In the illustrated embodiment, rack 230 includes two opposing receptacle holders 234 separated by heater holder 236. Receptacle holder 234 may comprise one or more flanges from which a receptacle may be hung. In the illustrated embodiment, each receptacle holder 234 comprises two flanges. However, in other embodiments, receptacle holder 234 may take another form, such as a chamber for holding a receptacle. Heater holder 236 is disposed between the two illustrated receptacle holders 134 and comprises a chamber for holding a heater. Finally, rack 230 also may include at least one collector chamber 238 below receptacle holder 234.

Figure 13:
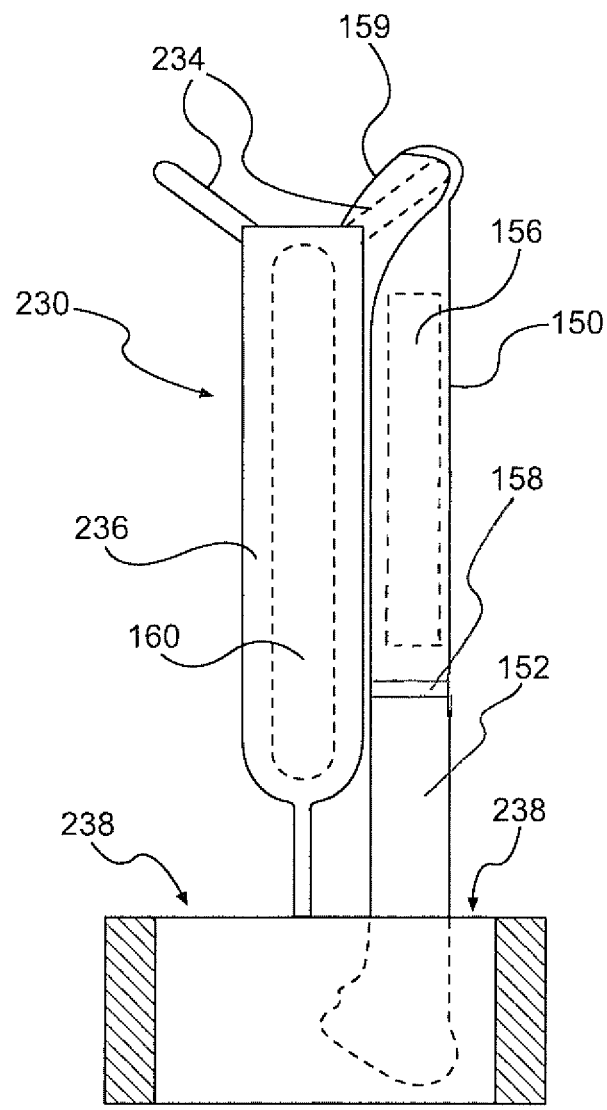
FIG. 13 is a profile view of the rack of FIG. 12, showing a receptacle mounted to the receptacle holder of the rack.

FIG. 13 illustrates rack 230 with one receptacle 150 mounted on one receptacle holder 234 of rack 230. It should be noted that this discussion equally applies to mounting receptacle 150 to receptacle holder 134 of rack 130 in the previously disclosed embodiments. As seen in FIG. 13, flap 159 of receptacle 150 is placed over receptacle holder 234 so that the flanges of receptacle holder 234 are in the pocket formed between flap 159 and the body of receptacle 150. Thus, receptacle 150 hangs from receptacle holder 234 with the bottom end of receptacle 150 "bunched up" and collected inside collector chamber 238, as discussed above. Furthermore, a heater is disposed inside heater holder 236. The heater inside heater holder 236 may be heater 160, as illustrated, heater 60, or any other suitable heat source including but not limited to an electric heat source.

As shown in FIG. 13, the body of receptacle 150 is in thermally conductive contact with heater holder 236 (although a small space is shown between receptacle 150 and heater holder 236 for drawing clarity, it is to be understood that receptacle 150 is in contact with heater holder 236). Furthermore, in the illustrated embodiment, heater holder 236 comprises an opening that allows heater 160 to directly contact receptacle 150 so that heater 160 is in direct thermal conductive contact with receptacle 150.

Figure 16:
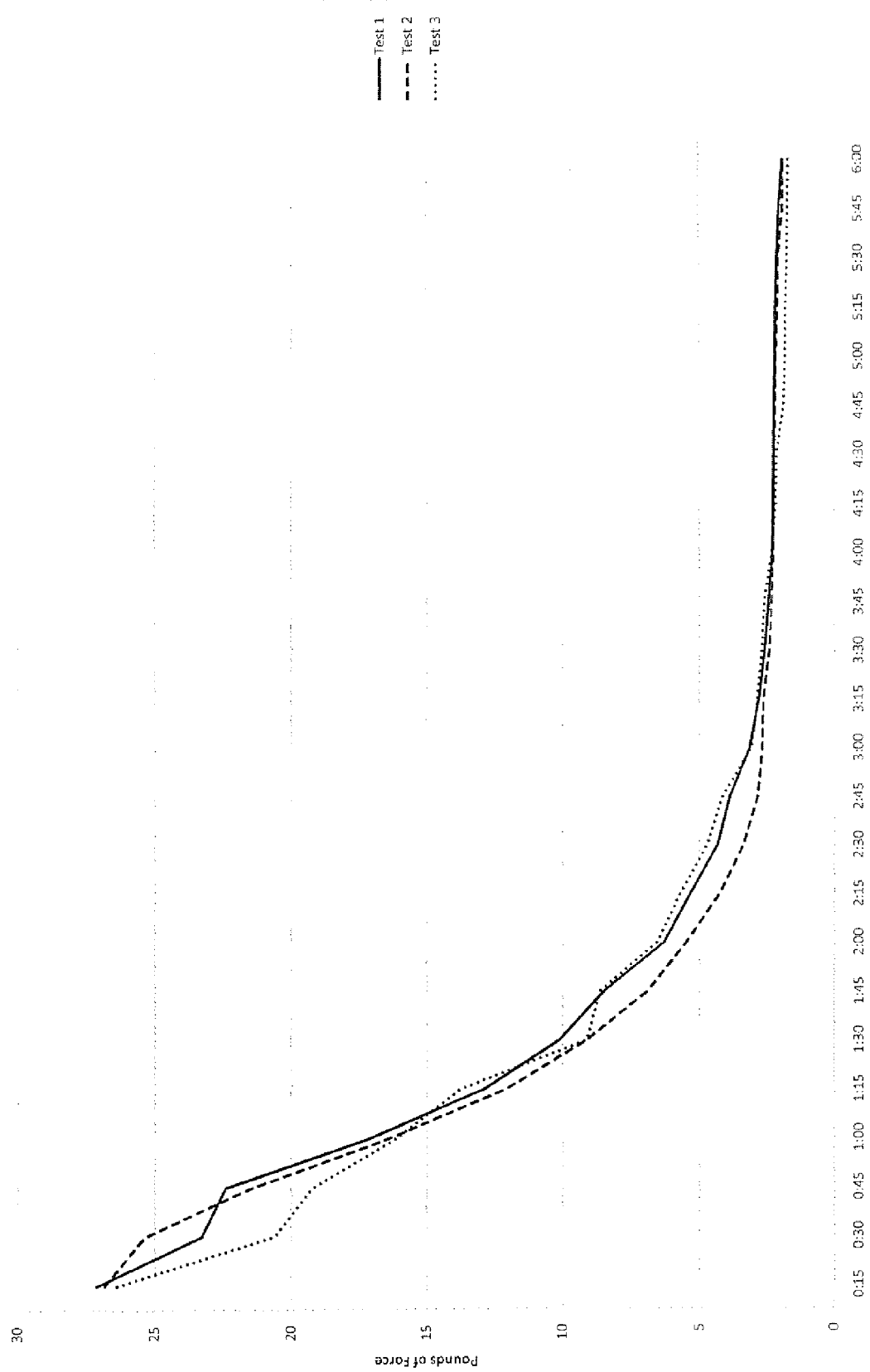
FIG. 16 is a chart showing effective force output over time for one embodiment of a heater pouch.

In order to increase heat transfer between heater 160 and receptacle 150, a compressive force may be applied to squeeze together heater 160 and receptacle 150. This compressive force may be provided by, for example, compression members 122 attached to the inside surface of outer shell 202 (or outer shell 102 in the previously disclosed embodiments). Alternatively, or additionally, the compressive force may be provided by heater 160 by regulating the pressure inside heater 160 with pressure regulator 162. This pressure regulation causes heater 160 to inflate and press against receptacle 150, thereby squeezing receptacle 150 against the inner surface of outer shell 202. It has been found that a force equivalent to the weight of a mass of between 1 kg and 12 kg of force may be exerted on receptacle 150 due to the inflation of heater 160. For example, FIG. 16 shows the force output over time for one embodiment of heated 60. However, greater and lesser amounts of force are also possible.

Figure 14:
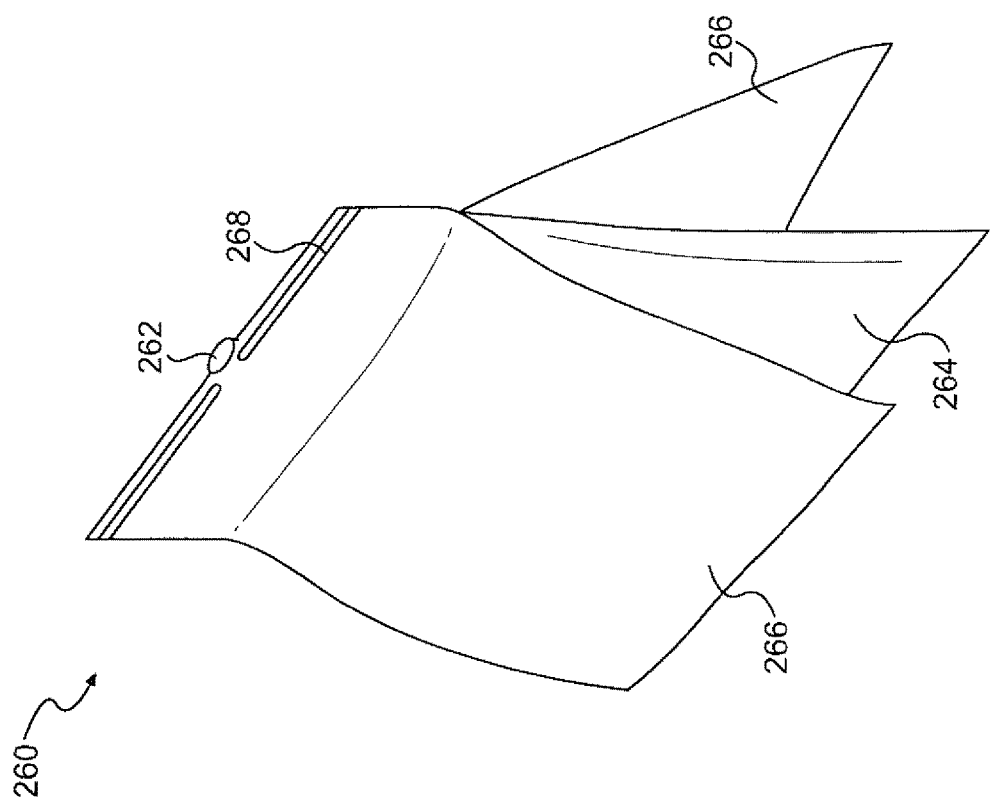
FIG. 14 is a perspective view of another embodiment of a heater.
Figure 15:
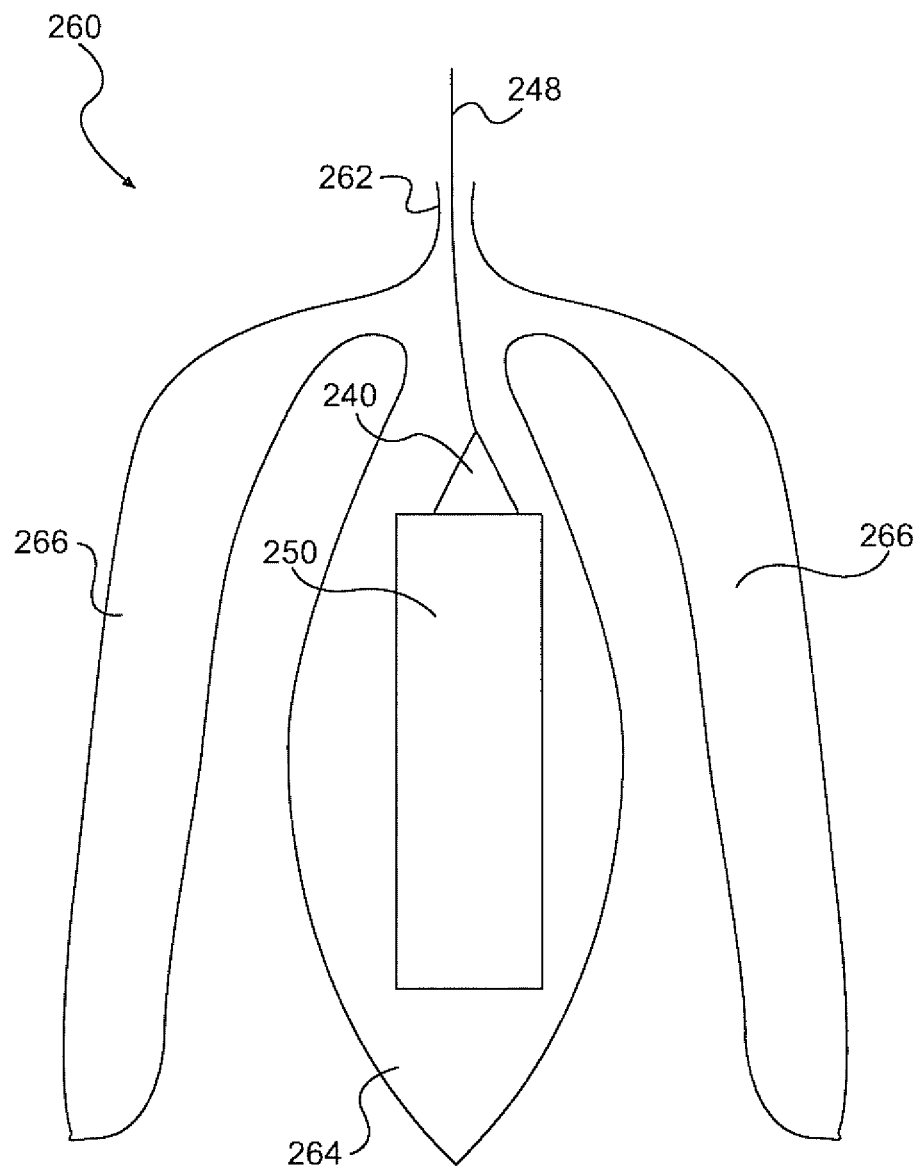
FIG. 15 is a cross-sectional view of the heater of FIG. 14.

Another embodiment of a heater is shown in FIGS. 14 and 15. In this embodiment heater 260 is a pouch with three leaves or chambers, namely central chamber 264 and lateral chambers 266. Central chamber 264 and lateral chambers 266 are all in fluid communication with one another. Sealed activator compartment 240 and reactant compartment 250 are disposed inside central chamber 264. Heater 260 further comprises seal 268 and pressure regulator 262 which allows reaction gases to escape in a controlled manner thereby maintaining a desired pressure inside central chamber 264 and lateral chambers 266. Thus, central chamber 264 and lateral chambers 266 inflate due to the reaction gases. When heater 260 is mounted to rack 230, it can be seen that central chamber 264 is disposed inside heater holder 236 and lateral chambers 266 hang over the top of receptacle holders 234 so that each receptacle 150 is sandwiched between one lateral chamber 266 and central chamber 264. Due to this configuration, receptacles 150 are compressed against central chamber 264 thereby improving heat transfer.

As seen in FIG. 15, sealed activator compartment 240 and reactant compartment 250 are disposed inside central chamber 264. In this embodiment, sealed activator compartment 240 is substantially identical in structure to sealed activator 40 discussed above. In particular, sealed activator compartment 240 is ruptured by pulling on middle shear strip 248 which extends out of heater 260 where it accessible by a user. However, unlike heater 60 disclosed above, in this embodiment the reactant compartment (reactant compartment 250) is an activator permeable pouch that is wrapped around sealed activator compartment 240. Thus, when sealed activator compartment 240 is ruptured by pulling on middle shear strip 248, activator immediately contacts and permeates reactant compartment 250 thereby setting off an exothermic reaction whose reaction gases inflate heater 260.

Throughout this disclosure, the terms "activator" and "reactant" may refer to two substances that when mixed together undergo an exothermic reaction. Examples of exothermic reactions that can be used include the combination of water with strong acids, combining alkalis and acids, polymerization, thermite reaction, aluminum-based reactions, magnesium-iron-based reactions, anhydride-based reactions, and so forth. One particularly suitable, non-toxic exothermic composition is Lava Gel® (manufactured by Forever Young International, Inc, Escondido, Calif., USA) which is known to exhibit a very controlled temperature for an extended period of time, with simply the addition of water or an electrolyte solution, such as saline water (as the activator). However, other activators and reactants may be used, according to design preference, including reactants that require activation or moderation by more than one activator compound or element. Furthermore, although the present disclosure in general contemplates exothermic reactions, it is of course possible to provide activators and reactants that undergo an endothermic reaction if the goal is to cool the receptacles rather than heat them.

An example of the method of using the presently disclosed embodiments will now be described. In this example, the heat activated substance in the receptacle is a therapeutic wax (such as paraffin, soy-based wax or vegetable based wax) or lotion that is solid at room temperature but melts if exposed to a heat source above the melting point temperature of the heat activated substance. The user first either opens the outer shell to expose the rack or removes the rack from the outer shell depending on the embodiment. The user hangs one or more receptacles containing the heat activated substance from the receptacle holder of the rack, with the substance chamber of the receptacle higher than the bottom of the treatment chamber of the receptacle. The user also places a heater inside the heater holder of the rack. The user then activates the heater (for example, by pulling a tab which ruptures an activator chamber, or by simply pouring activator into a heater pouch containing an exothermic reactant). The user then immediately closes the outer shell or replaces the outer shell over the rack.

Once the outer shell is in place, the user will see reaction gases (non-toxic, and mainly consisting of steam, though essential oils may be added to generate a pleasant and therapeutic vapor) escaping from the vent in the outer shell. An additional benefit these visible reaction gases is that they serve as an "automatic clock" for the device: Once the gases stop venting from the outer shell (approximately 5 minutes in some embodiments), the user knows the exothermic reaction is complete and that the heat activated substance has been in thermal conductive contact with the heater for sufficient time for the heat activated substance to melt and collect in the treatment chamber of the receptacle. The user then opens the outer shell to expose the rack, or removes the rack from the outer shell, and removes the receptacles from the rack. The user (or the person receiving the treatment) then places his or her hands (or feet, or other body part as the case may be) in the receptacles in order to receive therapeutic treatment from the now heated heat activated substance.

The materials used to construct a heated wax therapy treatment apparatus are not critical. However, in one embodiment, the outer shell and the rack may be made from a metal such as aluminum or steel. If the rack is made from a material that readily conducts heat, such as metal, heat transfer from the heater to the receptacles is improved. The heater and the receptacles may be made from a plastic pouch constructed from plastics such as polypropylene, polyethylene or biodegradable and/or compostable plastics. The receptacles may have a micro-taffeta inner surface in order to increase surface area. The heat activated substance inside the receptacles may be a wax or resin such as paraffin with a melting point of approximately 50° C.

The dimensions of the heated wax therapy treatment apparatus are also not critical. In one embodiment, the outer shell is approximately 31 cm in length and 13 cm in width at the widest point. The heater may be 20 cm in length and 16 cm in width. The heater holder of the rack, of course, has slightly larger dimensions than the heater in order to accommodate the heater. The receptacle may be 38 cm in length and 18 cm in width, and may contain between 30 to 100 g of heat activated substance, depending on the application. Finally, the rack may be approximately 23 cm in both length and depth and 9 cm in width. However, it is to be understood that these exemplary figures should not be considered limiting, as the presently disclosed embodiments may be constructed in any size.

There are numerous advantages provided by the presently disclosed embodiments. The disclosed embodiments provide for sanitary hot wax spa treatments because the therapy receptacles are only used by one person, thereby eliminating the problem of multiple people dipping their hands in a common vessel of melted wax.

Furthermore, the presently disclosed embodiments provide for very convenient spa treatments. No electricity is required, and the entire self-contained heated wax therapy treatment apparatus is portable. Thus, treatments may be provided any location, indoors or outdoors. The presently disclosed embodiments are also very safe. Unlike conventional spa treatments that require a potentially dangerous heat source such as a vessel of scalding hot water, the heater used in the presently disclosed embodiments is contained within the outer shell.

Further, because the melted wax collects at the bottom the treatment receptacle it does not remain in contact with the heater after it melts. Thus, the wax does not become dangerously hot. Additionally, there is no wasted wax as there is in conventional hot wax treatments where it is necessary to empty the common wax vessel routinely due to contamination. Finally, the receptacles used in the presently disclosed embodiments are disposable and may be constructed from biodegradable and/or compostable plastics.

What has been described above includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An apparatus for preparing a self-contained heated treatment receptacle for use by a subject, comprising:
   an outer shell comprising an inner surface;
   a rack disposed inside the outer shell, the rack comprising a receptacle holder and a heater holder;
   at least a first receptacle mounted to the receptacle holder of the rack, the at least first receptacle comprising a substance to be heated, wherein an outer wall surface of the at least first receptacle faces the heater holder and an opposite wall surface of the at least first receptacle faces the inner surface of the outer shell; and
   a gas generating heater in a chamber of the heater holder of the rack, wherein the heater further comprises a reactant mixable with an activator to produce an exothermic reaction that generates heat and gases that fill the heater;
   wherein the exothermic reaction and produced gases cause heat to flow to the at least first receptacle and heat the substance to be heated inside the at least first receptacle; and
   wherein a compression force is delivered by the heater to the outer surface of the at least first receptacle as the heater fills with the gases so that the opposite wall surface of the at least first receptacle is caused to be squeezed against an inner surface of the outer shell and is in thermal conductive contact with the heater.

2. The apparatus according to claim 1, wherein the outer shell comprises two halves hingedly connected to each other so as to expose the rack when the two halves of the outer shell are spread apart and conceal the rack when the two halves of the outer shell are closed, and wherein the receptacle holder comprises an outwardly extending flange mountable to a pocket of the at least first receptacle.

3. The apparatus according to claim 1, wherein the outer shell comprises an externally positioned vent operable to regulate the compression force exerted on the at least one receptacle by the heater by controlling egress of gases from the heater produced by the exothermic reaction, and wherein the substance to be heated is a solid wax that melts after the exothermic reaction is produced.

4. The apparatus according to claim 1, wherein the activator is separated from the reactant by a breakable barrier.

5. An apparatus for preparing a self-contained heated treatment receptacle for use by a subject, comprising:
   a rack disposed inside an outer shell;
   a first receptacle mounted to the rack, the first receptacle comprising a substance to be heated;
   an inflatable heater mounted in a chamber of the rack, the inflatable heater comprising activator and reactant mixable with each other to produce an exothermic reaction that generates heat and gases;
   wherein an outer wall surface of the first receptacle faces the inflatable heater and an opposite wall surface of the first receptacle faces away from the inflatable heater, and
   wherein gases produced by the exothermic reaction inflate the inflatable heater causing the heater to inflate and squeeze the first receptacle so a compressive force is delivered from the heater to the first receptacle so that at least one outer wall of the heater is conductively connected to the first receptacle causing heat to flow from the first receptacle and heat the substance to be heated.

6. The apparatus according to claim 5, wherein the inflatable heater is a pouch comprising a vent for expelling the gases produced by the exothermic reaction.

7. The apparatus according to claim 6, wherein the vent further comprises a pressure regulator that regulates the compression force exerted on the at least one receptacle by controlling expulsion of gases from the inflatable heater to maintain a target gas pressure inside the inflatable heater that results from the reactant reacting with the activator.

8. The apparatus according to claim 1, wherein the at least first receptacle further comprises at least two internal compartments separated by a barrier permeable to the substance to be heated after the substance to be heated is heated.

9. The apparatus according to claim 1,
   wherein the outer shell is a one-piece outer shell; and
   wherein the is rack vertically slidably and removably disposed inside the outer shell.

10. The apparatus according to claim 9, further comprising a pedestal that supports the rack and the one-piece outer shell, and wherein a substantially airtight seal is formed between the rack and the one-piece outer shell.

11. The apparatus according to claim 4, wherein the breakable barrier is shearable by pulling on a tab connected to the breakable barrier and extending outside of the heater.

12. The apparatus according to claim 11, the heater comprising:
   an outer impermeable containment envelope;
   a permeable pouch disposed in the envelope and comprising the reactant; and
   an activator compartment housing the activator, the activator compartment being disposed in the envelope and in communication with the tab.

13. The apparatus according to claim 12, further comprising:
   a plurality of outer strips being folded under the activator compartment with tips of the outer strips anchored inside the outer containment envelope; and
   a shear strip extending away from the activator compartment and attached to the tab.

14. The apparatus according to claim 5, further comprising a compression member disposed inside the outer shell, the outer shell delivering an additional compression force to squeeze together the inflatable heater and the at least first receptacle.

15. The apparatus according to claim 5, wherein the compressive force exerted on the at least first receptacle by the inflatable heater ranges between 5 lbs and 25 lbs and endures for at least five minutes.

16. The apparatus according to claim 5, the heater comprising:
   an outer impermeable containment envelope comprising a central chamber in fluid communication with a plurality of lateral chambers;
   a permeable pouch disposed in the central chamber and comprising the reactant; and
   an activator compartment housing the activator, the activator compartment being disposed in the envelope and in communication with a tab extending outside of the heater pouch and connected to a breakable barrier separating the activator from the reactant; and
   wherein the lateral chambers hang over the first receptacle, and wherein gases of the exothermic reaction inflate the lateral and central chambers so that the heater compresses against the first receptacle.

17. An apparatus for preparing a self-contained heated treatment receptacle for use by a subject, comprising:
   an outer shell comprising an inner surface;
   a rack disposed inside the outer shell, the rack comprising a receptacle holder and a heater holder;
   at least a first receptacle mounted to the receptacle holder of the rack, the at least first receptacle comprising a substance to be heated;
   a heater disposed in a chamber of the heater holder of the rack, wherein the heater further comprises a reactant mixable with an activator to produce an exothermic reaction that generates heat and gases that fill the heater; and
   a compression member disposed inside the outer shell for delivering a compression force that causes the heater and the at least first receptacle to be squeezed together;
   wherein an outer wall surface of the at least first receptacle faces the heater holder and an opposite wall surface of the at least first receptacle faces the compression member;
   wherein the exothermic reaction and generated gases cause heat to flow to the at least first receptacle and heat the substance to be heated inside the at least first receptacle;
   wherein the heater compresses against the at least one receptacle as the heater fills with the gases so that the at least first receptacle is in a sustained thermal conductive connection with the heater.

18. The apparatus according to claim 17, wherein the compression member is a rigid protrusion attached to an inner surface of the outer shell.

19. The apparatus according to claim 17, wherein the compression member is a compressible cushion.

* * * * *